United States Patent [19]

Tacker, Jr.

[11] Patent Number: 5,785,059
[45] Date of Patent: Jul. 28, 1998

[54] METHOD OF RELEASING CONDUCTIVE ELEMENTS FROM FIBROTIC TISSUE

[75] Inventor: Willis A. Tacker, Jr., Redmond, Wash.

[73] Assignee: InControl, Inc., Redmond, Wash.

[21] Appl. No.: 846,413

[22] Filed: Apr. 3, 1997

[51] Int. Cl.⁶ ................................................ A61B 17/50
[52] U.S. Cl. ................................................ 128/898; 607/1
[58] Field of Search .................. 607/1, 116; 128/898; 604/23, 26

[56] References Cited

U.S. PATENT DOCUMENTS

| | | | |
|---|---|---|---|
| 4,969,463 | 11/1990 | Dahl et al. | 607/5 |
| 5,207,683 | 5/1993 | Goode et al. | 606/1 |
| 5,330,481 | 7/1994 | Hood et al. | 128/898 |

Primary Examiner—William E. Kamm
Assistant Examiner—Kennedy J. Schaetzle
Attorney, Agent, or Firm—Richard O. Gray, Jr.

[57] ABSTRACT

A method is provided for removing an implanted cardiac lead having a lead body and at least one conductive electrode from a mammalian body. The method includes the steps of providing an indifferent electrode, establishing electrical contact between the indifferent electrode and the body, and providing a generator of electrical energy. The method further includes the steps of coupling the generator between the conductive electrode and the indifferent electrodes and causing the generator to apply electrical energy between the conductive electrode and the indifferent electrode. The energy has a magnitude sufficient to produce gas by electrolysis between the conductive electrode and fibrotic tissue grown around the electrode. Thereafter, the lead body is pulled in an anterior direction relative to the mammalian body to remove the cardiac lead from the mammalian body.

13 Claims, 2 Drawing Sheets

METHOD OF RELEASING CONDUCTIVE ELEMENTS FROM FIBROTIC TISSUE

BACKGROUND OF THE INVENTION

The present invention generally relates to a method of releasing a conductive element from fibrotic tissue within a mammalian body. More specifically, the present invention relates to such a method for use in removing a cardiac lead from a mammalian body, which lead includes at least one conductive electrode attached to fibrotic tissue within the body.

Implantable cardiac devices such as pacemakers and defibrillators are well-known in the art. Such devices are generally coupled to a patient's heart by one or more leads which are permanently implanted beneath the skin of the patient in the heart or a cardiac vein or artery of the patient's heart. Each lead includes at least one conductive electrode for making electrical contact with the heart.

After a lead has been implanted for a period of time, fibrotic tissue within the body grows around the lead. This fibrotic tissue growth is relied upon to eventually permanently fix the implanted lead in place. The period of time required for the fibrotic tissue to grow varies depending upon the lead location and the construction of the lead. When the fibrotic tissue grows, it not only grows around the implanted lead, but in addition, when the lead has a coiled electrode, such as a shocking electrode of a defibrillation lead, the fibrotic tissue can even grow in between the lead electrode coils.

At times, it is necessary to remove an implanted lead. Fibrotic tissue may have grown around most any portion of the lead including the insulation portions and the conductive electrode or electrodes. To extract the lead, the fibrotic tissue must be released from the lead. The fibrotic tissue can be released from the insulative materials, such as silicon, rubber or polyurethane, by pulling on the lead body. If pulling is not effective, various types of known devices may be used to separate the fibrotic tissue from the insulation materials. One such device is a sheath which surrounds the lead and has a leading cutting edge to core through the fibrotic tissue.

However, the conductive electrodes are more problematic. Those that have a coiled configuration are most problematic since the fibrotic tissue actually grows into the electrode coil. Further, when an electrode is located in an area distal to a required bend in the lead, such as in the coronary sinus of the heart, the separating of the electrode from the fibrotic tissue is even more difficult and not always possible with current devices and methods without the potential of serious complications.

SUMMARY OF THE INVENTION

The invention therefore provides a method of releasing a conductive element from fibrotic tissue of a mammalian body. The method includes the steps of providing an indifferent electrode, establishing electrical contact between the indifferent electrode and the body, and providing a generator of electrical energy. The method further includes the steps of coupling the generator between the conductive element and the indifferent electrode and causing the generator to apply electrical energy between the conductive element and the indifferent electrode, wherein the energy has a magnitude sufficient to produce gas by electrolysis between the conductive element and the fibrotic tissue.

The present invention further provides a method of releasing a conductive electrode carried by a cardiac lead implanted in a mammalian body from fibrotic tissue of the mammalian body. The method includes the steps of providing an indifferent electrode, establishing electrical contact between the indifferent electrode and the body, and providing a generator of electrical energy. The method includes the further steps of coupling the generator between the conductive electrode and the indifferent electrode and causing the generator to apply electrical energy between the conductive electrode and the indifferent electrode, wherein the energy has a magnitude sufficient to produce gas by electrolysis between the conductive electrode and the fibrotic tissue.

The present invention still further provides a method of removing a cardiac lead implanted in a mammalian body from fibrotic tissue wherein the lead has a lead body and at least one conductive electrode. The method includes the steps of providing an indifferent electrode and establishing electrical contact between the indifferent electrode and the body. The method further includes the steps of providing a generator of electrical energy and coupling the generator between the conductive electrode and the indifferent electrode. The method further includes the steps of causing the generator to apply electrical energy between the conductive electrode and the indifferent electrode, wherein the energy has a magnitude sufficient to produce gas by electrolysis between the conductive electrode and the fibrotic tissue, and thereafter, pulling on the lead in an anterior direction relative to the mammalian body to remove the cardiac lead from the mammalian body.

BRIEF DESCRIPTION OF THE DRAWINGS

The features of the present invention which are believed to be novel are set forth in particularity in the appended claims. The invention, together with further aspects and advantages thereof, may best be understood by making reference to the following description, taken in conjunction with the accompanying drawings, in the several figures of which like reference numerals identify identical elements, and wherein:

DETAILED DESCRIPTION OF THE PREFERRED EMBODIMENT

Figure 1:
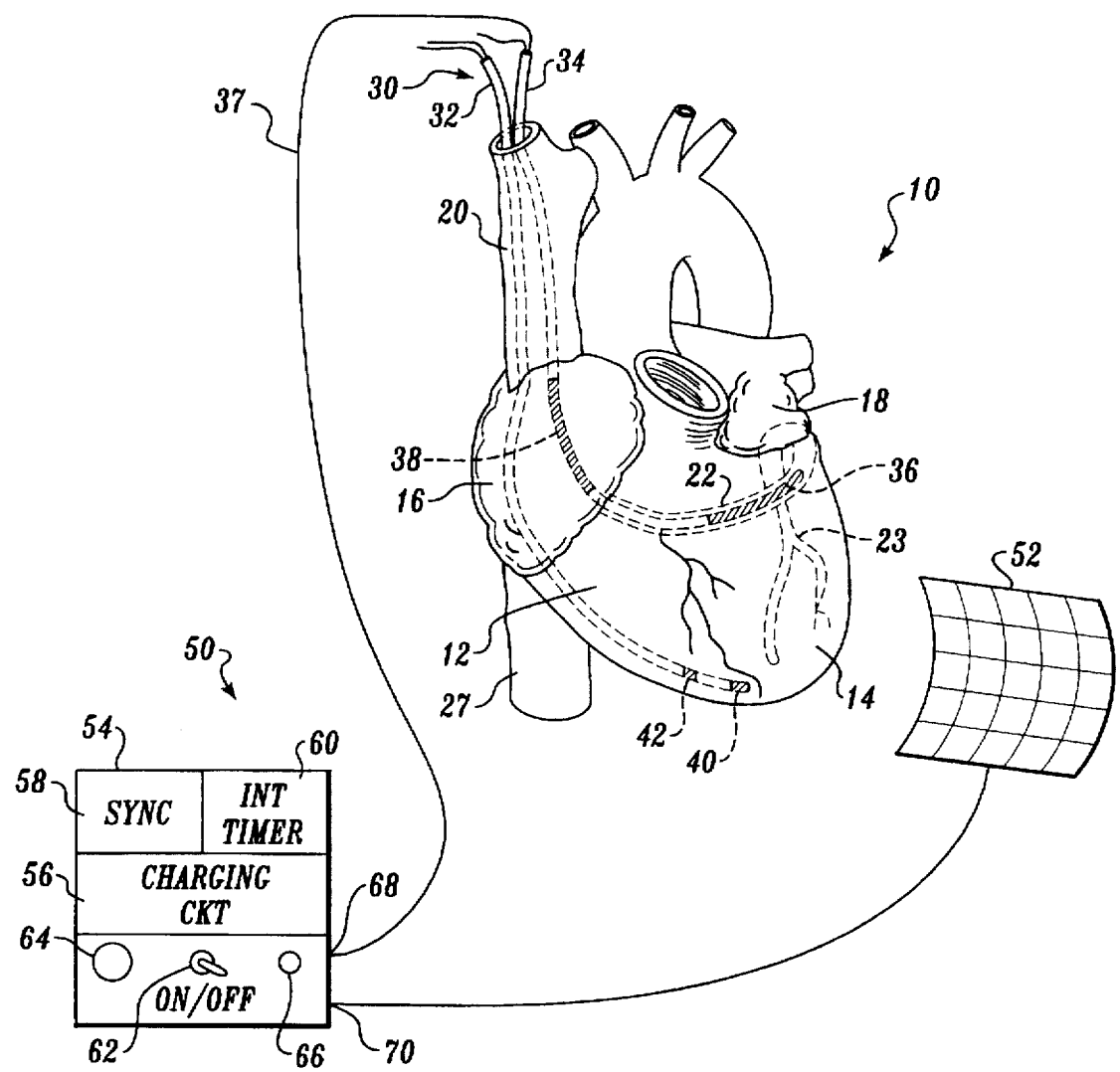
FIG. 1 is a schematic representation of a human heart having a pair of cardiac leads implanted therein and a system which may be used for releasing conductive electrodes of the leads from fibrotic tissue in accordance with the method of the present invention.

Referring now to FIG. 1, it illustrates a heart 10 having a lead system 30 implanted therein. The portions of the heart particularly illustrated are the right ventricle 12, the left ventricle 14, the right atrium 16, the left atrium 18, the superior vena cava 20, the coronary sinus 22 which communicates with the great vein 23, and the inferior vena cava 27. The lead system 30 includes an endocardial lead 32 and an intravascular lead 34. The intravascular lead 34 includes an elongated distal coil electrode 36 and a proximal elongated coil electrode 38. The electrodes 36 and 38 are spaced apart such that when the elongated electrode 36 is within the coronary sinus 22 the proximal electrode 38 is within the right atrium as illustrated. The endocardial lead 32 includes an electrode sensing pair including a distal sensing electrode 40 and proximal sensing electrode 42. The electrodes 40 and 42, as illustrated, reside within the right ventricle 18 of the heart.

The lead system 30 is particularly adapted for use with an implantable atrial defibrillator as described, for example, in U.S. Pat. No. 5,348,021 which issued on Sep. 20, 1994 in the names of John M. Adams, Clifton A. Alferness, and Kenneth R. Infinger, and which patent is assigned to the assignee of the present invention and incorporated herein by reference. As described in that patent, the electrodes 36 and 38 serve a dual purpose for both sensing atrial activity to support the detection of atrial fibrillation and for applying cardioverting electrical energy to the atria for cardioverting atrial fibrillation. To that end, the electrodes 36 and 38 are elongated in configuration and are coiled in construction. The sensing electrode pair of electrodes 40 and 42 of endocardial lead 32 may be used for sensing ventricular activity of the heart. Such sensing may be used to support interval timing as described, for example, in U.S. Pat. No. 5,207,219 which issued on May 4, 1993 in the names of John M. Adams, Clifton A. Alferness, Kenneth R. Infinger, and Joseph M. Bocek, and which patent is assigned to the assignee of the present invention and incorporated herein by reference. As described in that patent, when the atria of the heart are in need of cardioversion, the cardioverting electrical energy is applied to the heart when the time between immediately successive ventricular activations (R waves) is greater than a predetermined minimum time interval. This assures that the cardioverting electrical energy is applied at a time when the heart is least vulnerable to the potential of induced ventricular fibrillation.

To best illustrate the method of the present invention, it will be assumed that explantation or extraction of the intravascular lead 34 is required. To that end, FIG. 1 further illustrates a system 50 which may be utilized for practicing the present invention to release electrodes 36 and 38 from fibrotic tissue which may have grown around the leads. As will be seen subsequently, the description with respect to FIGS. 2 through 4 will be directed in particular to the release of electrode 36 from fibrotic tissue within the coronary sinus 22.

The system 50 generally includes an indifferent or dispersive electrode 52 and a generator of electrical energy 54. The generator 54 more particularly includes a charging circuit 56, a synchronizing circuit 58, and an interval timer circuit 60. An on/off switch 62 is provided for turning the generator on and off. Further, the generator 54 includes a control 64 for adjusting the magnitude of the output electrical energy of the generator 54 and a push button actuator 66 which enables the delivery of electrical energy from the outputs 68 and 70 of the generator 54.

The intravascular lead 34 includes a conductor 37 which is electrically connected to the electrode 36. As can be noted from FIG. 1, the conductor 37 is coupled to the output 68 of the generator 54 for coupling the output 68 of generator 54 to the electrode 36. The output 70 of the generator 54 is coupled to the indifferent electrode 52.

In accordance with the broader aspects of the present invention, the conductive electrode 36 is released from the fibrotic tissue which may have grown around and in the electrode 36 by applying electrical energy from the generator 54 between the electrode 36 and the indifferent electrode 52. The energy utilized, in accordance with the present invention, has a magnitude sufficient to produce gas by electrolysis between the conductive electrode or element 36 and the fibrotic tissue which may have grown around and in the electrode 36. To that end, the indifferent electrode 52 forms a return path for the electrical energy and may comprise of a large surface area patch electrode electrically contacting the skin of the patient or any other form of indifferent electrode which would provide such a return path.

The electrical energy applied between the conductive electrode 36 and the indifferent electrode 52 has a finite duration of between, for example, 2 and 20 milliseconds. The energy is preferably applied in synchronism with an R wave of the heart which may be detected by the electrodes 40 and 42 or by a surface electrogram. The synchronizing circuit 58 is provided to assure that the energy is not applied until the presence of an R wave.

The electrical energy is also applied only when the interval between successive R waves is greater than a predetermined minimum interval as described in the aforementioned U.S. Pat. No. 5,207,219. To that end, the interval timer 60 is provided within the generator 54.

When the electrical energy is to be applied between the electrode 36 and the indifferent electrode 52, the generator is turned on with the on/off switch 62. The energy level is then selected using control 64 which causes the charging circuit 56 to charge an internal capacitor to a predetermined voltage. When the capacitor is fully charged, the enable button 62 is pushed to activate the synchronization circuit 58 and the interval timing circuit 60. When an R wave appears which follows its immediately preceding R wave by a time greater than a predetermined time interval, the generator will then apply the electrical energy between the electrode 36 and the indifferent electrode 52.

The electrical energy may have many different waveforms. For example, the electrical energy may be applied in single or multiple pulses of monophasic direct current or single or multiple pulses of biphasic current or combinations thereof. The amount of energy required to produce adequate gas by electrolysis between the conductive electrode 36 and the indifferent electrode 52 depends largely upon the surface area of the electrode to be released from the fibrotic tissue. Defibrillation electrodes, such as electrodes 36 and 38 may require energies in the range of 1 joule to 10 joules to support the production of the gas by electrolysis. Pacing and sensing electrodes, such as electrodes 40 and 42 of endocardial lead 32, may require energies in the range of ½ joules to 5 joules to cause the production of gas by electrolysis.

Higher energies may also be utilized for providing additional separation effects. For example, at higher energies than mentioned above, shock waves can be produced which can provide a mechanical aspect to the separation process. To produce such shock waves for defibrillation electrodes, energies in the range of 10 joules to 250 joules may be utilized and for pacing or sensing electrodes, energies in the range of 5 joules to 50 joules may be utilized.

To provide additional and further separation effects, still higher energies may be utilized to produce arcs to provide localized burning of the fibrotic tissue. For defibrillation electrodes, energies in excess of 250 joules may be utilized to produce such arcs and for pacing and sensing electrodes, energies greater than 50 joules may be utilized to produce such arcs.

Figure 2:
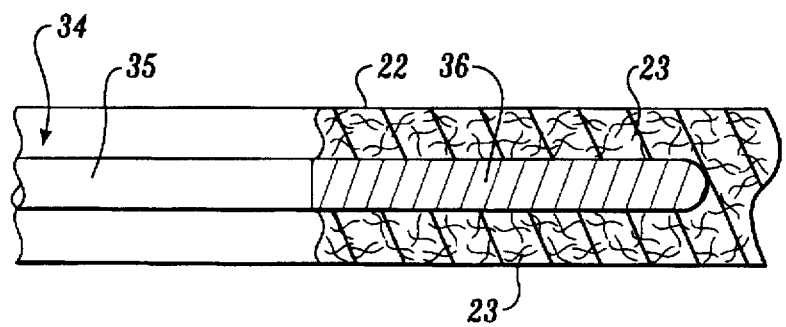
FIG. 2 is a partial, cross-sectional view, to an enlarged scale, of the electrode 36 of lead 34 and the coronary sinus 22 of the heart of FIG. 1 illustrating the fibrotic tissue growth around the electrode prior to implementation of the method of the present invention.

Referring now to FIG. 2. it illustrates fibrotic tissue 23 which has grown around and potentially even into the elongated coiled defibrillation electrode 36 within the coronary sinus 22. As can be more clearly seen in FIG. 2. the electrode 36 is carried by a lead body 35 of lead 34. As can be seen in FIG. 2. the fibrotic tissue 23 has grown entirely around and along the entire length of the electrode 36.

Figure 3:
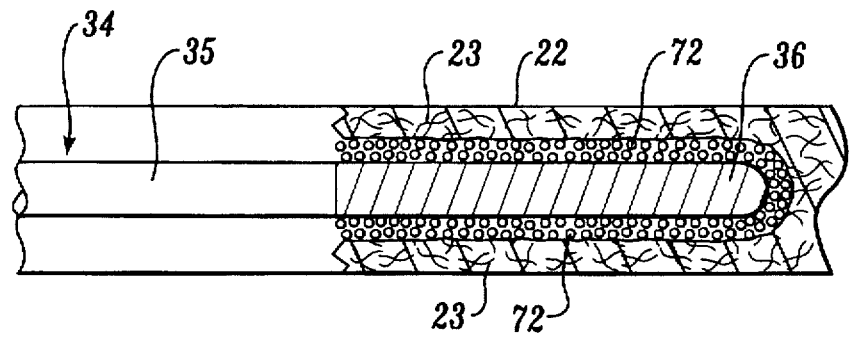
FIG. 3 is a partial, cross-sectional view, similar to that of FIG. 2, illustrating the release of the fibrotic tissue from the electrode 36 during the implementation of the method of the present invention.

Referring now to FIG. 3. it illustrates the separation of the fibrotic tissue 23 from the electrode 36 during the application of the electrical energy between the electrode 36 and the indifferent electrode 52 (FIG. 1). Here it can be seen that gas in the form of bubbles 72 is produced by electrolysis between the conductive electrode 36 and the fibrotic tissue 23 to cause the electrode 36 to be released from the fibrotic tissue 23. As previously mentioned. energies in the range of 1 joule to 10 joules may be utilized to produce the gas bubbles 72 by electrolysis.

Figure 4:
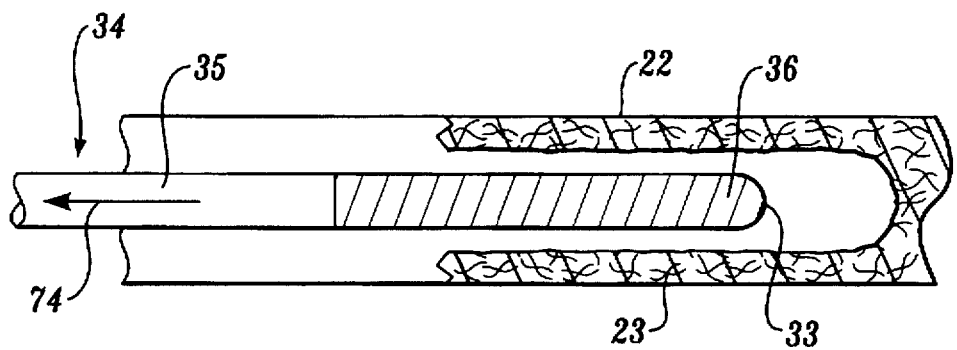
FIG. 4 is a partial, cross-sectional view, similar to FIGS. 2 and 3 illustrating the removal of the lead 34 from the coronary sinus of the heart after the fibrotic tissue has been released from the electrode 36.

Once the electrical energy has been applied between the conductive electrode 36 and the indifferent electrode 52. the lead may then be explanted from the patient's heart and, more particularly, the patient's coronary sinus 22 as illustrated in FIG. 4. Here it can be clearly seen that the fibrotic tissue 23 has been separated from the electrode 36 so that the electrode 36 is released from the fibrotic tissue 23. To remove the lead from the coronary sinus 22 and thus the patient's heart, the lead body 35 of lead 34 may be pulled in an anterior direction as indicated by the arrow 74 to explant the lead. Preferably, a locking stylet. of the type well known in the art, is fed through a central stylet coil of the lead 34 to engage and grip the lead body 35 at its distal end 33. Thereafter, and in a known manner, the lead body 35 may be pulled from the patient's heart from the lead body distal end 33.

As can be seen from the foregoing. the present invention provides a new and improved method for releasing a conductive element from fibrotic tissue of a mammalian body such as a human body. More particularly, the present invention provides a new and improved method which may be employed to advantage for removing a cardiac lead implanted in a heart even though fibrotic tissue may have grown around and even in a conductive electrode of the cardiac lead. Since the release of the conductive electrodes from fibrotic tissue is achieved by the application of electrical energy between the conductive electrodes and an indifferent electrode. electrodes which may be located in areas or regions of the heart which have proven in the past to be difficult for removal, may be removed with relative ease. Once such particular application for the method of the present invention is for the removal of an elongated defibrillation electrode from the coronary sinus of the human heart.

While a particular embodiment of the present invention has been shown and described, modifications may be made, and it is therefore intended to cover in the appended claims, all such changes in modifications which fall within the true spirit and scope of the invention.

What is claimed is:

1. A method of releasing a conductive element from fibrotic tissue of a mammalian body. the method including the steps of:

providing an indifferent electrode;

establishing electrical contact between the indifferent electrode and the body;

providing a generator of electrical energy;

coupling the generator between the conductive element and the indifferent electrode; and causing the generator to apply electrical energy between the conductive element and the indifferent electrode, the energy having a magnitude sufficient to produce gas by electrolysis between the conductive element and the fibrotic tissue.

2. A method as defined in claim 1 wherein the causing step includes selecting the energy to be between one-half joule and two hundred and fifty joules.

3. A method of releasing a conductive electrode carried by a cardiac lead implanted in a mammalian body from fibrotic tissue of the mammalian body. the method including the steps of:

providing an indifferent electrode;

establishing electrical contact between the indifferent electrode and the body;

providing a generator of electrical energy;

coupling the generator between the conductive electrode and the indifferent electrode;

causing the generator to apply electrical energy between the conductive electrode and the indifferent electrode, the energy having a magnitude sufficient to produce gas by electrolysis between the conductive electrode and the fibrotic tissue.

4. A method as defined in claim 3 wherein the causing step includes selecting the energy to be between one-half joule and two hundred and fifty joules.

5. A method of removing a cardiac lead implanted in a mammalian body from fibrotic tissue. the lead having a lead body and at least one conductive electrode, the method including the steps of:

providing an indifferent electrode;

establishing electrical contact between the indifferent electrode and the body;

providing a generator of electrical energy;

coupling the generator between the conductive electrode and the indifferent electrode;

causing the generator to apply electrical energy between the conductive electrode and the indifferent electrode. the energy having a magnitude sufficient to produce gas by electrolysis between the conductive electrode and the fibrotic tissue; and thereafter, pulling on the lead body in an anterior direction relative to the mammalian body to remove the cardiac lead from the mammalian body.

6. A method as defined in claim 5 wherein the causing step includes selecting the energy to be between one-half and two hundred and fifty joules.

7. A method as defined in claim 5 wherein the causing step includes selecting the energy to be between one-half joule and five joules.

8. A method as defined in claim 5 wherein the causing step includes selecting the energy to be between five joules and fifty joules.

9. A method as defined in claim 5 wherein the causing step includes selecting the energy to be between one joule and ten joules.

10. A method as defined in claim 5 wherein the causing step includes selecting the energy to be between ten joules and fifty joules.

11. A method as defined in claim 5 wherein the lead body has a distal end and wherein the pulling step includes pulling on the lead body from the lead body distal end.

12. A method as defined in claim 5 wherein the causing step further includes detecting cardiac R waves and causing the generator to apply the electrical energy in synchronism with an R wave.

13. A method as defined in claim 5 wherein the causing step further includes detecting cardiac R waves and causing the generator to apply the electrical energy when a minimum time period is completed since a last detected R wave.

* * * * *